(12) United States Patent
Rahme et al.

(10) Patent No.: US 10,990,193 B2
(45) Date of Patent: Apr. 27, 2021

(54) SYSTEM AND METHOD FOR MEDICAL IMAGING REPORT INPUT

(71) Applicant: Imaging Advantage LLC, Phoenix, AZ (US)

(72) Inventors: Kamil Rahme, Phoenix, AZ (US); Danyell Wilt, Phoenix, AZ (US)

(73) Assignee: Imaging Advantage LLC, Phoenix, AZ (US)

( * ) Notice: Subject to any disclaimer, the term of this patent is extended or adjusted under 35 U.S.C. 154(b) by 0 days.

(21) Appl. No.: 16/533,225

(22) Filed: Aug. 6, 2019

(65) Prior Publication Data

US 2019/0361538 A1 Nov. 28, 2019

Related U.S. Application Data

(63) Continuation of application No. 15/416,775, filed on Jan. 26, 2017, now Pat. No. 10,401,975.

(Continued)

(51) Int. Cl.

| | |
|---|---|
| *G06F 3/023* | (2006.01) |
| *G16H 30/20* | (2018.01) |
| *G06F 3/038* | (2013.01) |
| *H04N 5/00* | (2011.01) |
| *G10L 15/26* | (2006.01) |
| *G16H 30/40* | (2018.01) |
| *G16H 10/60* | (2018.01) |
| *G16H 15/00* | (2018.01) |

(52) U.S. Cl.
CPC ............ *G06F 3/023* (2013.01); *G06F 3/0231* (2013.01); *G06F 3/038* (2013.01); *G10L 15/26* (2013.01); *G16H 30/20* (2018.01); *G16H 30/40* (2018.01); *H04N 5/00* (2013.01); *G16H 10/60* (2018.01); *G16H 15/00* (2018.01)

(58) Field of Classification Search
CPC ........ G16H 15/00; G16H 30/00; G16H 30/20; G16H 30/40; G16H 80/00; G06F 19/321; G06F 3/023
See application file for complete search history.

(56) References Cited

U.S. PATENT DOCUMENTS 5,740,801 A * 4/1998 Branson ................ G06F 19/321
128/920
5,938,607 A * 8/1999 Jago ......................... A61B 8/00
600/437

(Continued)

*Primary Examiner* — Alvin H Tan
(74) *Attorney, Agent, or Firm* — Kilpatrick Townsend & Stockton LLP

(57) ABSTRACT

According to some embodiments of the invention, improved systems and methods for medical imaging report input are provided. A zero footprint software extension is provided that interfaces with supported hardware devices, such as dictation devices. The extension may be agnostic to different medical facilities and different medical imaging systems. Radiologists may quickly populate medical imaging reports with existing structured data included in the EMRs or other forms, such as medical orders. Radiologists may also use voice recognition technology in conjunction with the dictation devices to fill in diagnoses and other relevant information in the medical imaging reports. The functionality of the dictation devices may be configured by the radiologists to meet their preferences and needs, either generally or with respect to a specific medical imaging report.

20 Claims, 7 Drawing Sheets

Related U.S. Application Data

(60) Provisional application No. 62/287,244, filed on Jan. 26, 2016.

(56) References Cited

U.S. PATENT DOCUMENTS

| | | | | |
|---|---|---|---|---|
| 6,909,378 B1 * | 6/2005 | Lambrechts | .......... | G06F 3/0238 340/4.32 |
| 7,116,310 B1 * | 10/2006 | Evans | ................... | G06F 3/0238 345/156 |
| 7,170,422 B2 * | 1/2007 | Nelson | ................... | G08C 19/28 340/10.32 |
| 7,266,777 B2 * | 9/2007 | Scott | ....................... | G08C 17/02 348/734 |
| 8,098,140 B1 * | 1/2012 | Escobosa | .................. | G06F 8/65 340/12.22 |
| 8,949,427 B2 * | 2/2015 | Dubbels | ................ | G06F 9/5038 709/226 |
| 2002/0174206 A1 * | 11/2002 | Moyer | ................. | G06F 9/4411 709/221 |
| 2011/0028194 A1 * | 2/2011 | Tang | ................... | G06F 3/03543 463/1 |

* cited by examiner

SYSTEM AND METHOD FOR MEDICAL IMAGING REPORT INPUT

CROSS-REFERENCES TO RELATED APPLICATIONS

This application is a continuation of U.S. patent application Ser. No. 15/416,775, filed Jan. 26, 2017, which claims the benefit of U.S. Provisional Patent Application No. 62/287,244, filed Jan. 26, 2016, entitled "SYSTEM AND METHOD FOR MEDICAL IMAGING REPORT INPUT," each of which is hereby incorporated by reference in its entirety.

BACKGROUND OF THE INVENTION

Medical facilities, including hospitals and clinics, implement a variety of medical imaging systems, such as X-rays, CTs, MRIs, ultrasounds, and the like, to create medical images of patients. These medical images may be combined with patient information (e.g., name, date of birth, historical medical records, etc.) as well as imaging information (e.g., type of imaging, body location of imaging, name and location of medical facility, etc.) to create EMRs (electronic medical records). The EMRs may then be sent to radiologists, who may analyze and interpret the medical images. The radiologists may generate a medical imaging report including analysis and information (e.g., diagnoses, findings, conclusions, radiologist name, date and time of diagnoses, comments, etc.) that may be forwarded back to the medical facilities for appropriate treatment of the patients.

Implementing these processes may give rise to a variety of obstacles. For example, medical facilities may store EMRs (electronic medical records) on different systems that often have different protocols. Furthermore, medical imaging that is included in EMRs is often received from a variety of medical imaging systems (e.g., X-rays, CTs, MRIs, etc.) having different manufacturers, models, and years of manufacture. Sharing and distributing EMRs having immense variations creates obstacles to doctors collaborating on patient care. For example, radiologists may need a number and variety of different types of software to receive, interpret and transmit EMRs and medical imaging reports to and from different medical facilities and/or different medical imaging systems.

Amongst the different types of software used by radiologists, dictation software and apparatuses remains popular for completing analyses of medical images to generate medical imaging reports. Conventionally, radiologists receive the EMRs, interpret the medical imaging, and speak the results, along with any other relevant accompanying information, into the dictation apparatuses. Recordings of the dictations may then be sent by the radiologists to medical transcriptionists, who transcribe the information into a medical imaging report formatted according to the requirements of the prescribing medical facilities. By adding a third party (i.e., a medical transcriptionist) to the process, delays, increased costs and a higher incidence of error may be experienced in generating and processing medical imaging reports. These barriers can negatively impact patient care.

SUMMARY OF THE INVENTION

Thus, according to some embodiments of the invention, improved systems and methods for medical imaging report input are provided. According to some embodiments of the invention, a zero footprint software extension is provided that interfaces with supported hardware devices, such as dictation devices (referred to herein interchangeably as "recording devices"). The extension may be agnostic to different medical facilities and different medical imaging systems. In other words, EMRs received from different medical facilities and/or created by different medical imaging systems may be converted to and displayed in a common format. Radiologists may quickly populate medical imaging reports with existing structured data included in the EMRs or other forms, such as medical orders. Radiologists may also use voice recognition technology in conjunction with the dictation devices to fill in diagnoses and other relevant information in the medical imaging reports. The functionality of the dictation devices may be configured by the radiologists to meet their preferences and needs, either generally or with respect to a specific medical imaging report.

According to some embodiments of the invention, a radiological system for reviewing medical imaging in a browser environment is provided. The radiological system comprises an input port configured to couple to a dictation device including a microphone and a plurality of tactile inputs. The radiological system further comprises a display port configured to couple to a display. The radiological system further comprises a computing device communicatively coupled to both the display and the dictation device. The computing device loads a browser application coupled to an applet hosted on remote hub located away from the computing device, loads code into the browser application to facilitate communication between the dictation device and the applet, identifies the dictation device coupled to the computing device from within the browser application, determines a device image that corresponds to the input device, selects the matching device image from a plurality of device images that correspond to a plurality of input devices, outputs the matching device image to the display port, wherein the matching device image includes one or more graphical representations corresponding to the one or more tactile inputs of the dictation device; outputs, to the display port, a map corresponding to the matching device image, the map including a listing of the one or more tactile inputs of the dictation device and a listing of one or more actions assignable to the one or more tactile inputs, wherein each of the one or more actions corresponds to an input to the computing device; receives a first user input corresponding to a first tactile input of the one or more tactile inputs of the dictation device via the input port; assigns a first action of the one or more actions to the first tactile input in response to the first user input; outputs a medical imaging report to the display port; receives a second user input from the first tactile input of the one or more tactile inputs of the dictation device via the input port; and amends the medical imaging report in the browser application according to the first action in response to receiving the second user input from the first tactile input.

According to some embodiments of the invention, a method is provided. The method comprises identifying, by a computing device, an input device, wherein the input device includes a microphone and one or more tactile inputs. The method further comprises selecting, by the computing device, a matching device image that corresponds to the input device, wherein the matching device image is selected from a plurality of device images that correspond to a plurality of input devices. The method further comprises rendering, by the computing device, the matching device image to a display coupled to the computing device, wherein the matching device image includes one or more graphical representations corresponding to the one or more tactile inputs of the input device. The method further comprises rendering, by the computing device to the display, a map corresponding to the matching device image, the map including a listing of the one or more tactile inputs of the input device and a listing of one or more actions assignable to the one or more tactile inputs, wherein each of the one or more actions corresponds to an input to the computing device. The method further comprises receiving, by the computing device, a first user input corresponding to a first tactile input of the one or more tactile inputs of the input device. The method further comprises assigning, by the computing device, a first action of the one or more actions to the first tactile input in response to the first user input. The method further comprises rendering, by the computing device, a medical imaging report to the display. The method further comprises receiving, by the computing device, a second user input from the first tactile input of the one or more tactile inputs of the input device. The method further comprises amending, by the computing device, the medical imaging report according to the first action in response to receiving the second user input from the first tactile input.

According to some embodiments of the invention, a computer-program product tangibly embodied in a non-transitory machine-readable storage medium of a computing device is provided. The non-transitory machine-readable storage medium includes instructions that, when executed by one or more processors, cause the one or more processors to identify an input device, wherein the input device includes a microphone and one or more tactile inputs; select a matching device image that corresponds to the input device, wherein the matching device image is selected from a plurality of device images that correspond to a plurality of input devices; render the matching device image to a display coupled to the computing device, wherein the matching device image includes one or more graphical representations corresponding to the one or more tactile inputs of the input device; render, to the display, a map corresponding to the matching device image, the map including a listing of the one or more tactile inputs of the input device and a listing of one or more actions assignable to the one or more tactile inputs, wherein each of the one or more actions corresponds to an input to the computing device; receive a first user input corresponding to a first tactile input of the one or more tactile inputs of the input device; assign a first action of the one or more actions to the first tactile input in response to the first user input; render a medical imaging report to the display; receive a second user input from the first tactile input of the one or more tactile inputs of the input device; and amend the medical imaging report according to the first action in response to receiving the second user input from the first tactile input.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

BRIEF DESCRIPTION OF THE DRAWINGS

Illustrative embodiments of the present invention are described in detail below with reference to the following drawing figures.

DETAILED DESCRIPTION OF THE INVENTION

Figure 1:
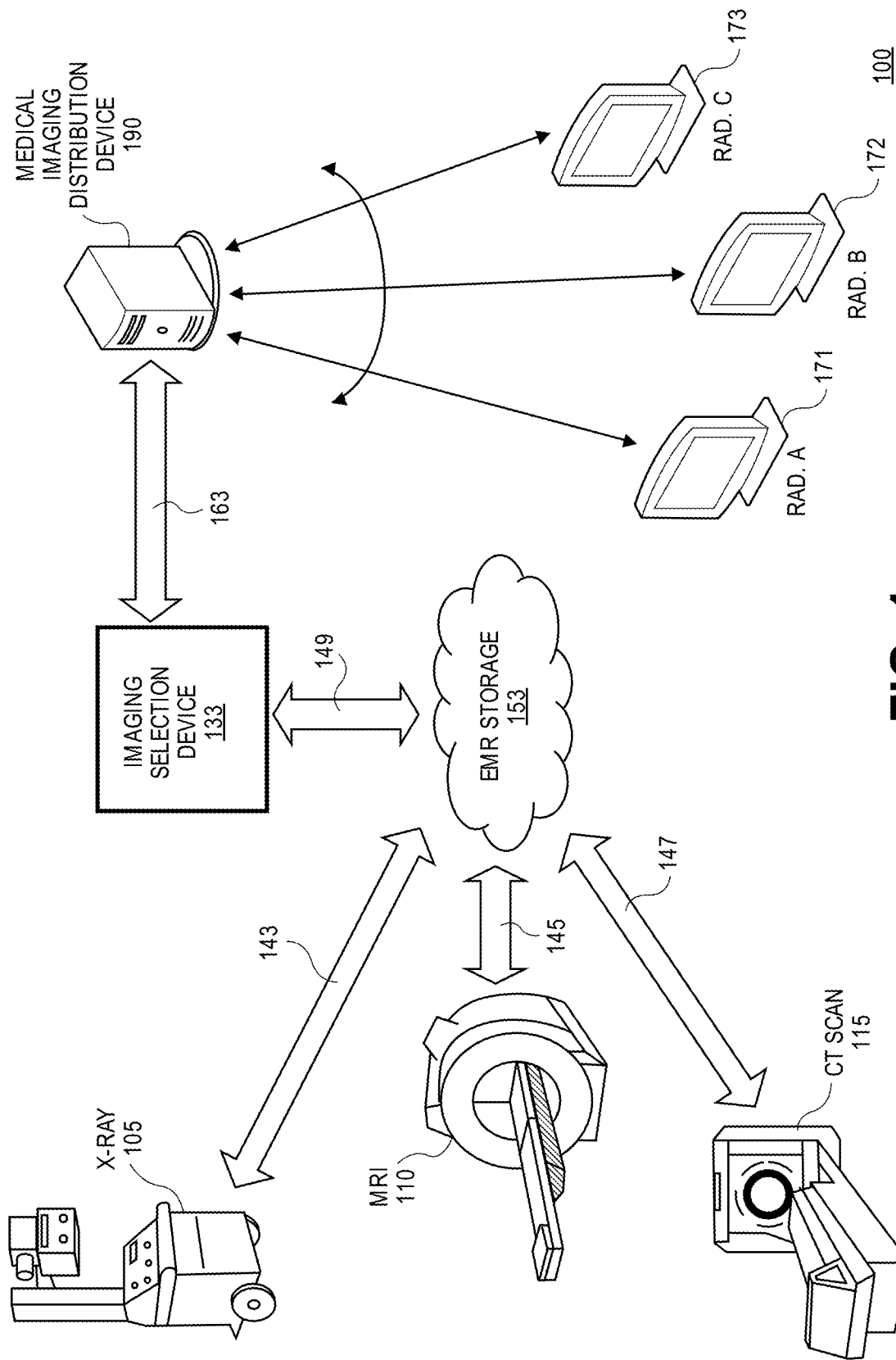
FIG. 1 is a system diagram illustrating a medical imaging distribution system according to some embodiments of the invention.

Certain aspects and embodiments of this disclosure are provided below. Some of these aspects and embodiments may be applied independently and some of them may be applied in combination as would be apparent to those of skill in the art. In the following description, for the purposes of explanation, specific details are set forth in order to provide a thorough understanding of embodiments of the invention. However, it will be apparent that various embodiments may be practiced without these specific details. The figures and description are not intended to be restrictive.

The ensuing description provides exemplary embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

The term "computer-readable medium" includes, but is not limited to, portable or non-portable storage devices, optical storage devices, and various other mediums capable of storing, containing, or carrying instruction(s) and/or data. A computer-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as compact disk (CD) or digital versatile disk (DVD), flash memory, memory or memory devices. A computer-readable medium may have stored thereon code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, or the like.

Furthermore, embodiments may be implemented by hardware, software, firmware, middleware, microcode, hardware description languages, or any combination thereof. When implemented in software, firmware, middleware or microcode, the program code or code segments to perform the necessary tasks (e.g., a computer-program product) may be stored in a computer-readable or machine-readable medium. A processor(s) may perform the necessary tasks.

FIG. 1 illustrates a system 100 for distributing EMRs (electronic medical records) that include medical imaging. System 100 includes medical imaging devices. The medical imaging devices may include, but are not limited to, X-ray device 105, MRI device 110, and CT scan device 115. Other types of medical imaging devices (not shown) include ultrasound devices, endoscopy devices, elastography devices, tactile imaging devices, thermography devices, medical photography devices, nuclear medicine functional imaging devices (e.g., positron emission tomography (PET) devices, single-photo emission computed tomography (SPECT) devices, etc.), and/or the like. System 100 also includes care system 153, imaging selection device 133, medical imaging distribution device 190, and radiology terminals 171, 172, and 173.

In the illustrated embodiment, X-ray device 105 is networked to care system 153 via link 143. Similarly, MRI device 110 is networked to care system 153 via link 145 and CT scan device 115 is networked to care system 153 via link 147. Links 143, 145, 147 may include Ethernet connections, wireless connections, or any other suitable network and/or networking protocol. For example, links 143, 145, 147 may be implemented as part of a personal area network (PAN), a local area network (LAN), a metropolitan area network (MAN), a wide area network (WAN), a storage area network (SAN), an enterprise private network (EPN), a virtual private network (VPN), and/or the like. Links 143, 145, 147 may represent communication via any suitable network protocol, such as WiFi/WiMAX, Bluetooth, fibre channel network protocols, TCP/IP, OSI, SSH, SMB, FTP, SMTP, HTTP, HTTPs, SSL, SFTP, and/or the like.

Care system 153 may include a networked datastore suitable to store EMRs, medical imaging, patient information, and the like, such as network-attached storage (NAS) or the like. Care system 153 may include, for example, EMR storage, a Picture Archiving and Communication System (PACS), a Radiology Information System (RIS), and/or the like. In some embodiments, care system 153 is a data storage server connected to a network that provides access to EMRs and other records by clients, such as medical facilities, doctors, patients, caregivers, and/or radiologists. Care system 153 may provide access to EMRs and other records using network file sharing protocols such as Network File System (NFS) protocol, Server Message Block (SMB)/Common Internet File System (CIFS) protocol, and/or Apple Filing Protocol (AFP). Care system 153 may include redundant memory backups to ensure the integrity of the EMRs. The networked datastore may have Terabytes of storage, for example. Care system 153 may include, for example, primary storage, secondary storage, tertiary storage, and/or offline storage. Care system 153 may further include processors, in some embodiments.

Imaging selection device 133 is configured to access care system 153 and medical imaging stored in care system 153. Imaging selection device 133 is configured to read EMRs stored in care system 153 as well as write to EMRs stored in care system 153 via link 149. Link 149 may include Ethernet connections, wireless connections, or other suitable networking protocol that facilitates read and/or write access to the particular care system 153.

X-ray device 105, MRI device 110, CT scan device 115, care system 153, and imaging selection device 133 may all be included in a same medical facility such as a hospital or clinic. Alternatively, the medical imaging devices may be in use at more than one clinic while care system 153 is not co-located at the same physical site of the medical imaging devices. In other words, care system 153 may be located locally or remotely with respect to a medical facility. Thus, it is contemplated that more than one care system 153 may be implemented in some embodiments.

Imaging selection device 133 is configured to access medical imaging files within care system 153 as well as certain medical data that is germane to analyzing medical imaging. Some medical data that is included in EMRs stored in care system 153 is not germane to medical imaging files. For example, a patient's social security number is not necessarily useful in analyzing medical imaging. Imaging selection device 133 sends medical imaging files and other relevant medical data that is relevant to analyzing medical imaging to medical imaging distribution device 190, via link 163. Medical imaging distribution device 190 may be a cloud server physically located at a datacenter in some embodiments. System 100 may include more than one distribution device 190 that are stored in different regional locales, for example. Imaging selection device 133 may access the distribution device 190 that is within closest physical proximity to the imaging selection device 133 in some embodiments. In some embodiments, imaging selection device 133 may select a distribution device 190 according to some other criteria, such as network traffic at particular distribution devices 190.

Distribution device 190 receives the medical images and other relevant medical data and generates a task to be put into a task list. The task includes the medical images and other medical data that would be useful in analyzing the medical images and generating a radiology report. The task is assigned to a radiologist and then transferred to the device/system (e.g. 171, 172, or 173) used by the assigned radiologist via one of network links 193. The server may assign the task to a certain radiologist based on radiology specialty (e.g., neurology, oncology, etc.), radiologist availability, a number of tasks already in a radiologist queue, or a variety of other factors.

The assigned radiologist will generate a report based on viewing the medical images and corresponding relevant medical data and send the report back to distribution device 190, via link 193. Distribution device 190 transmits the report back to imaging selection device 133. The report may be in a designated (e.g., standardized) format for efficient processing by imaging selection device 133. Imaging selection device 133 stores the report in care system 153 so that it is accessible for health care providers, facilities, caregivers, patients, etc., that may have access to care system 153.

Figure 2:
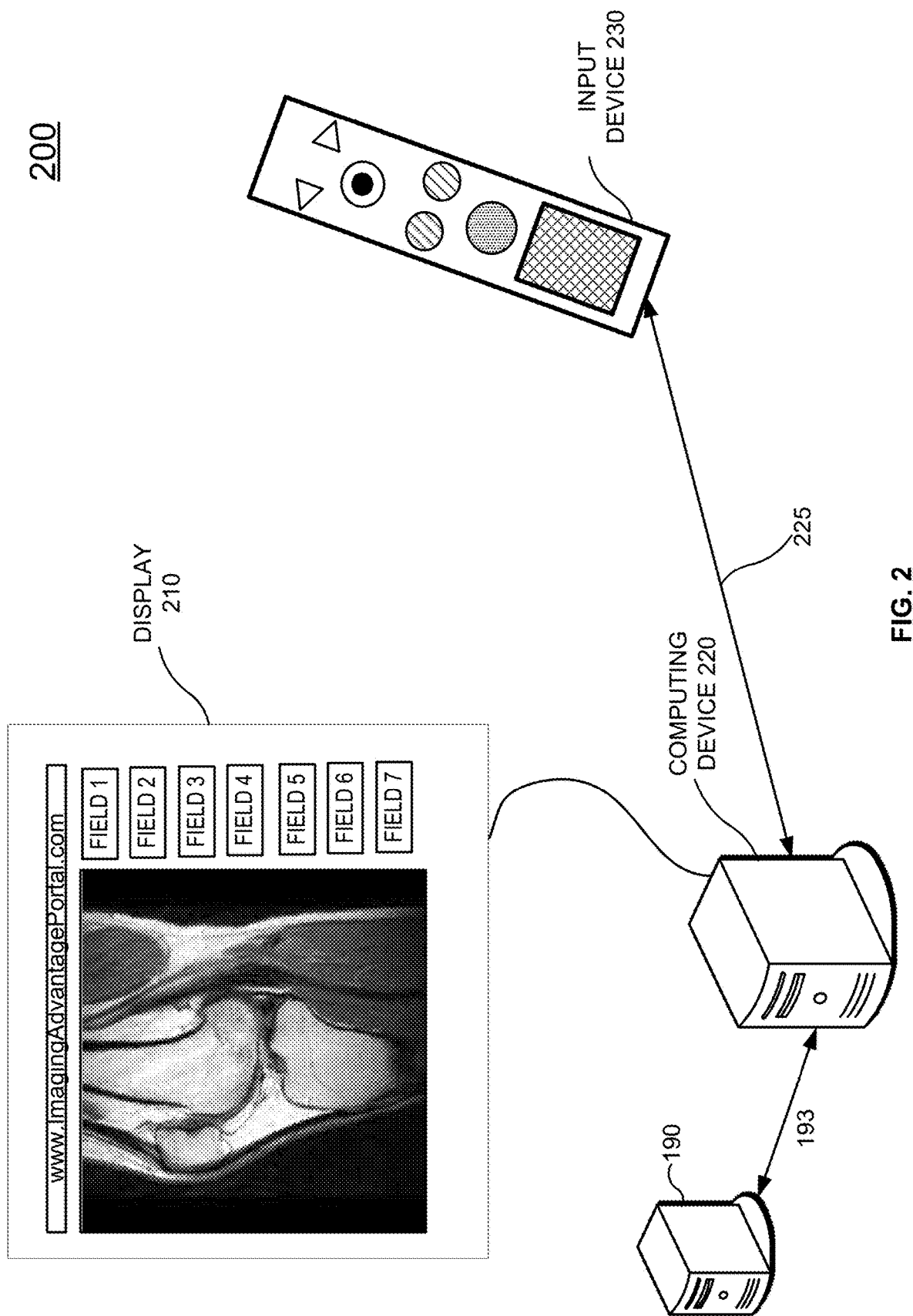
FIG. 2 is a system diagram illustrating a medical imaging report input system according to some embodiments of the invention.

FIG. 2 illustrates a medical imaging report input system 200 that includes one or more displays 210, a computing device 220, and an input device 230. System 200 is one example of a terminal that a radiologist may use to generate a medical imaging report to be appended to an EMR. Input device 230 may be communicatively coupled to computing device 220 via communication link 225. Communication link 225 may be wired (e.g., USB) or wireless (e.g., WiFi, BlueTooth, etc.).

Display(s) 210 may include one or more monitors (e.g., flat screen monitors) that are connected to computing device 220, which may be a computer tower. Computing device 220 includes processing logic (e.g., processor, microprocessor, FPGA, or other suitable logic device). Computing device 220 may also include a memory for storing medical imaging files (at least temporarily) and medical imaging reports. The medical imaging reports may also be stored in medical imaging distribution device 190, which is in communication with computing device 190 via network link 193. In one implementation, display 210 and computing device 220 are integrated into a desktop computer, a laptop computer, a netbook, a tablet computer, or a mobile device (e.g., a smart phone, a wearable device, etc.).

Computing device 220 may use any suitable number of subsystems to facilitate the functions described herein. Such subsystems or components may be interconnected via a system bus. Subsystems may include a printer, keyboard, fixed disk (or other memory comprising computer readable media), display 210, which may be coupled to a display adapter, and others. Peripherals and input/output (I/O) devices, which may couple to an I/O controller, can be connected to the computing device 220 by any number of means. For example, an external interface can be used to connect the computing device 220 to a WAN such as the Internet, input device 230, or a scanner. The interconnection via the system bus may allow the central processor to communicate with each subsystem and to control the execution of instructions from system memory or the fixed disk, as well as the exchange of information between subsystems. The system memory and/or the fixed disk may embody a computer-readable medium.

The functions of computing device 220 described herein may be implemented as software code to be executed by a processor using any suitable computer language such as, for example, Java, C++, or Perl, using, for example, conventional or object-oriented techniques. The software code may be stored as a series of instructions or commands on a computer-readable medium, such as a random access memory (RAM), a read only memory (ROM), a magnetic medium such as a hard drive or a floppy disk, and/or an optical medium such as a CD-ROM. The computer readable medium may be any combination of such storage or transmission devices.

Such programs may also be encoded and transmitted using carrier signals adapted for transmission via wired, optical and/or wireless networks conforming to a variety of protocols, including the Internet. As such, a computer-readable medium according to an embodiment of the present invention may be created using a data signal encoded with such programs. Computer-readable media encoded with the program code may be packaged with a compatible device or provided separately from other devices (e.g., via Internet download). Any such computer-readable medium may reside on or within a single computer product (e.g., a hard drive a CD, or an entire computer system), and may be present on or within different computer products within a system or network. The system may include display 210 for providing any of the results described herein to a user.

Input device 230 includes at least one microphone for voice input purposes. Input device 230 may be a USB (Universal Serial Bus) HID (Human Interface Device) input device. In some embodiments, computing device 220 includes a USB port and input device 230 is plugged into the USB port of computing device 220. In one embodiment, input device 230 is a Philips LFH5276. Input device 230 may be, in some embodiments, a recording device and/or a dictation device.

Computing device 220 may render medical imaging files of EMRs to display 210 for a radiologist to analyze. As will be discussed in more detail below, a radiologist may populate fields of a medical imaging report by speaking into the microphone of input device 230. The radiologist may also make other inputs to the medical imaging report by interacting with tactile inputs (e.g. buttons, trackpad, trackball) of input device 230.

When a given input device 230 is connected to computing device 220, computing device 220 may identify the input device 230. In some embodiments, input device 230 may send the computing device 220 a device identifier (in a bit string, for example) via communication link 225. Computing device 220 may identify the input device 230 according to the device identifier. Once computing device 220 identifies the input device 230, it may determine whether the identified input device 230 is a "trusted" or supported input device. In some embodiments, computing device 220 may compare the device identifier with a list of "trusted" or supported device identifiers stored on medical imaging distribution device 190. In some embodiments, computing device 220 may store a list of device identifiers that are "trusted" or supported. Computing device 220 may compare a device identifier received from input device 230 to a list of the trusted or supported device identifiers stored in memory of the computing device 220. Computing device 220 may send the device identifier to medical imaging distribution device 190 and receive a device image in return that is a graphical, pictorial and/or symbolic image of the trusted or supported device associated with that device identifier. Computing device 220 may also store device images of each of the trusted or supported devices. As used herein, a "trusted" device may be a device registered with the computing device 220. As used herein, a "supported" device may be a device capable of interfacing with the computing device 220 (e.g., an installed device, a device having a driver installed on computing device 220, a device for which a driver can be obtained, etc.).

Figure 3:
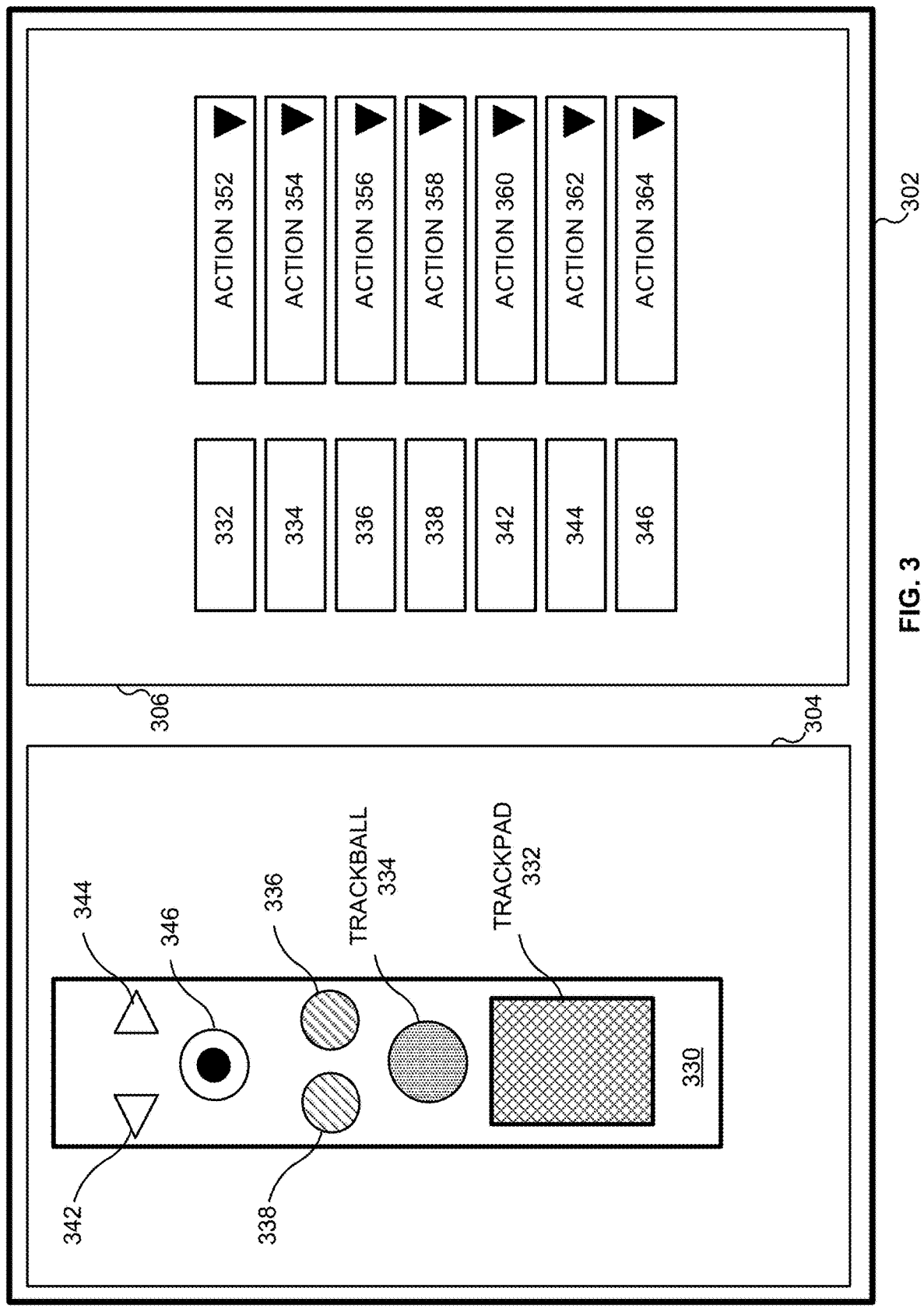
FIG. 3 is a graphical user interface (GUI) illustrating an input device and associated configuration dashboard according to some embodiments of the invention.

FIG. 3 illustrates an exemplary graphical user interface (GUI) 302 including a device image 304 and an interface action map 306 rendered on a display (e.g., display 210 of FIG. 2). In FIG. 3, device image 304 may correspond to an identified (and trusted or supported) input device 330, in the illustrated embodiment. Input device 330 is one example of input device 230. Input device 330 includes exemplary tactile inputs 332, 334, 336, 338, 342, 344, and 346. Tactile input 332 may be a trackpad or a touchpad. Tactile input 334 may be a trackball. Tactile inputs 336, 338, 342, 344, and 346 may be buttons in the illustrated embodiment. Although FIG. 3 includes buttons, trackpads, and trackballs, tactile inputs may also include other types of inputs, including capacitive sensing inputs, resistive sensing inputs, switches, or any other tactile inputs that receive inputs from users.

Device image 304 may match input device 330 in that it is a graphical, pictorial and/or symbolic representation of the input device 330 and includes the tactile inputs of input device 330. Device image 304 may be rendered on a display, such as display 210. Device image 304 may be rendered simultaneously with or separately from interface action map 306 on one or more displays 210, in combination or separately. Interface action map 306 may give a user the ability to map buttons on input device 230 to actions of input to the computing device 220. For example, the input actions may correspond to amendments of a medical imaging report displayed on display 210. In another example, the input actions may correspond to any functionality of the computing device, such as browser functionality, underlying web functionality, etc.

In the illustrated embodiment, interface action map 306 includes a listing of each tactile input of input device 330 on the left of interface action map 306. A corresponding action is assigned to each tactile input to the right of the listing of the tactile input. For example, action 352 is assigned to tactile input 332, in the illustrated embodiment. Action 352 may be changed by a user. In one implementation where interface action map 306 is rendered to a display, a user may select a specific action to assign to tactile input 332 by selecting the action from a drop-down menu. A user may use a computer mouse or keyboard to select the action to assign to the corresponding tactile input, in one embodiment. The actions assigned to the tactile inputs may be saved by the user to a user profile that is stored at medical imaging distribution device 190. Although shown and described in a particular configuration, it is contemplated that tactile inputs 332-346 and actions 352-364 may be displayed in any location, order, and/or configuration.

Example actions that can be assigned to tactile inputs of the input device 330 include starting an audio recording that will be converted to text using voice recognition software and populating a field of a medical imaging report, as well as stopping an audio recording that will be converted to text and populating a field of a medical imaging report. Example actions specific to a medical imaging report may also include digitally signing a dictation that has been converted to text to populate a field of a medical imaging report. Signing the dictation may include accessing and saving a previously saved digital signature into the medical imaging report. One action assigned to a tactile input may include digitally signing a text version of a dictation and opening a next dictation session. In one embodiment, an action includes digitally signing and closing a first medical imaging report and opening a next medical imaging report. Other actions may include finding a medical imaging report, navigating fields in a medical imaging report, inserting structured data from another report (e.g., an EMR) into a medical imaging report, sending a medical imaging report for review, putting a medical imaging report on hold, and the like. Actions 352-364 may each be different, or some or all of actions 352-364 may be the same, according to the radiologist's preferences.

In one embodiment, the action assigned to a tactile input is rendering a support request menu for requesting support to assist in further analysis of the medical imaging. A request generation may request additional information (e.g., additional medical imaging or medical information) from electronic medical records stored in care system 153. In one embodiment, the action assigned to a tactile input is contacting a referring physician or other medical provider that is familiar with the medical imaging. In this case, the radiologist may be connected to the referring physician over VoIP, the Internet, or any other communication channel.

Figure 4A:
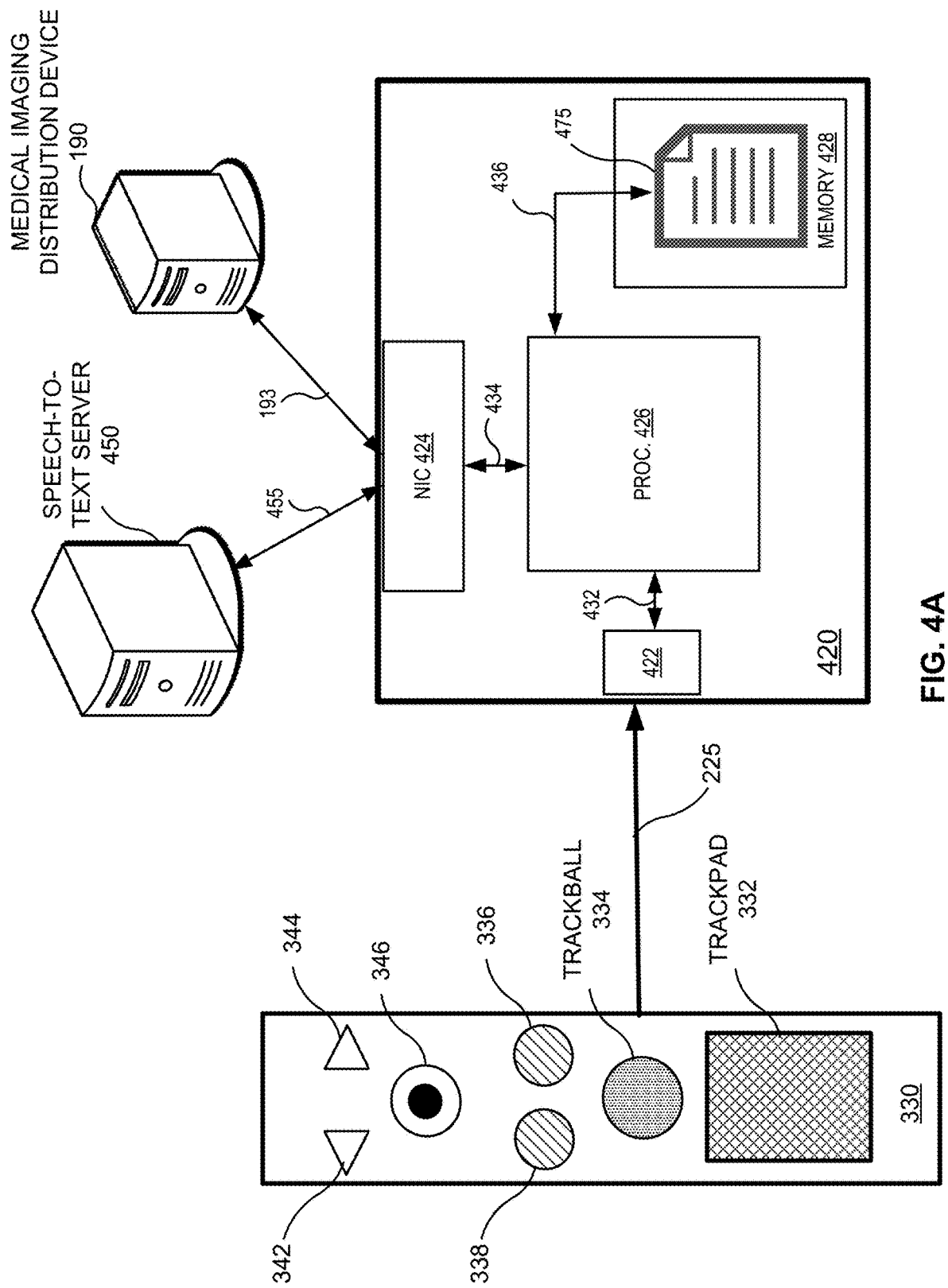
FIG. 4A is a system diagram illustrating a medical imaging report processing system according to some embodiments of the invention.

FIG. 4A illustrates a block diagram schematic of a computing device 420, input device 330, speech-to-text server 450, and medical imaging distribution device 190. Computing device 420 includes a communication port 422, a NIC (Network Interface Card) 424, processing logic 426, and a memory 428. Communication port 422 may be a USB port. Processing logic 426 may be a processor, microprocessor, FPGA, or other suitable logic device. Memory 428 may be a flash memory or a spinning hard drive. Memory 428 may store a medical imaging report 475. Memory 428 is communicatively coupled to processing logic 426 by way of interface 436. Communication port 422 is communicatively coupled to processing logic 426 by way of interface 432. NIC 424 is communicatively coupled to processing logic 426 by way of interface 434.

In one embodiment, a radiologist may press a tactile input button 346 and input device 330 records a dictation of the radiologist. The dictation may be streamed to computing device 420 through communication port 422 to processing logic 426. Processing logic 426 may then send the dictation stream to speech-to-text server 450 via NIC 424. NIC 424 may packetize the dictation stream for transmission to speech-to-text server 450. It is understood that a communication channel 455 between server 450 and NIC 424 may include any type of network, including local area networks (LANs), wide area networks (WANs), and/or the Internet and that server 450 may be physically remote from computing device 420 or proximate to computing device 420.

Speech-to-text server 450 may analyze the dictation stream, convert it to text, and send it back to processing logic 426 by way of NIC 424. Processing logic may render the text to a display (e.g., display 210) viewable by the radiologist. The radiologist may review the text, and, if satisfactory, approve the dictation text for populating a field of medical imaging report 475. To approve (sign) the text generated by the dictation, the radiologist may simply push a button (e.g., tactile input button 338) of input device 330 which causes the dictation text to be saved to medical imaging report 475. As referenced previously, medical imaging report 475 may be stored locally in memory 428 or stored in a memory in medical imaging distribution device 190, which may be a server located proximately or remotely. The dictation text may be saved to medical imaging report 475 to be RIS (Radiology Information System) compatible. If medical imaging report 475 is stored locally, once the medical imaging report is completed by the radiologist, the radiologist may actuate a tactile input button (e.g., 336) to sign, save, and transmit the medical imaging record to medical imaging distribution device 190. In this case, processing logic 426 accesses medical imaging report 475 from memory 428 and sends it to medical imaging distribution device 190 via NIC 424. Device 190 may then send it back to care system 153 via imaging selection device 133.

Figure 4B:
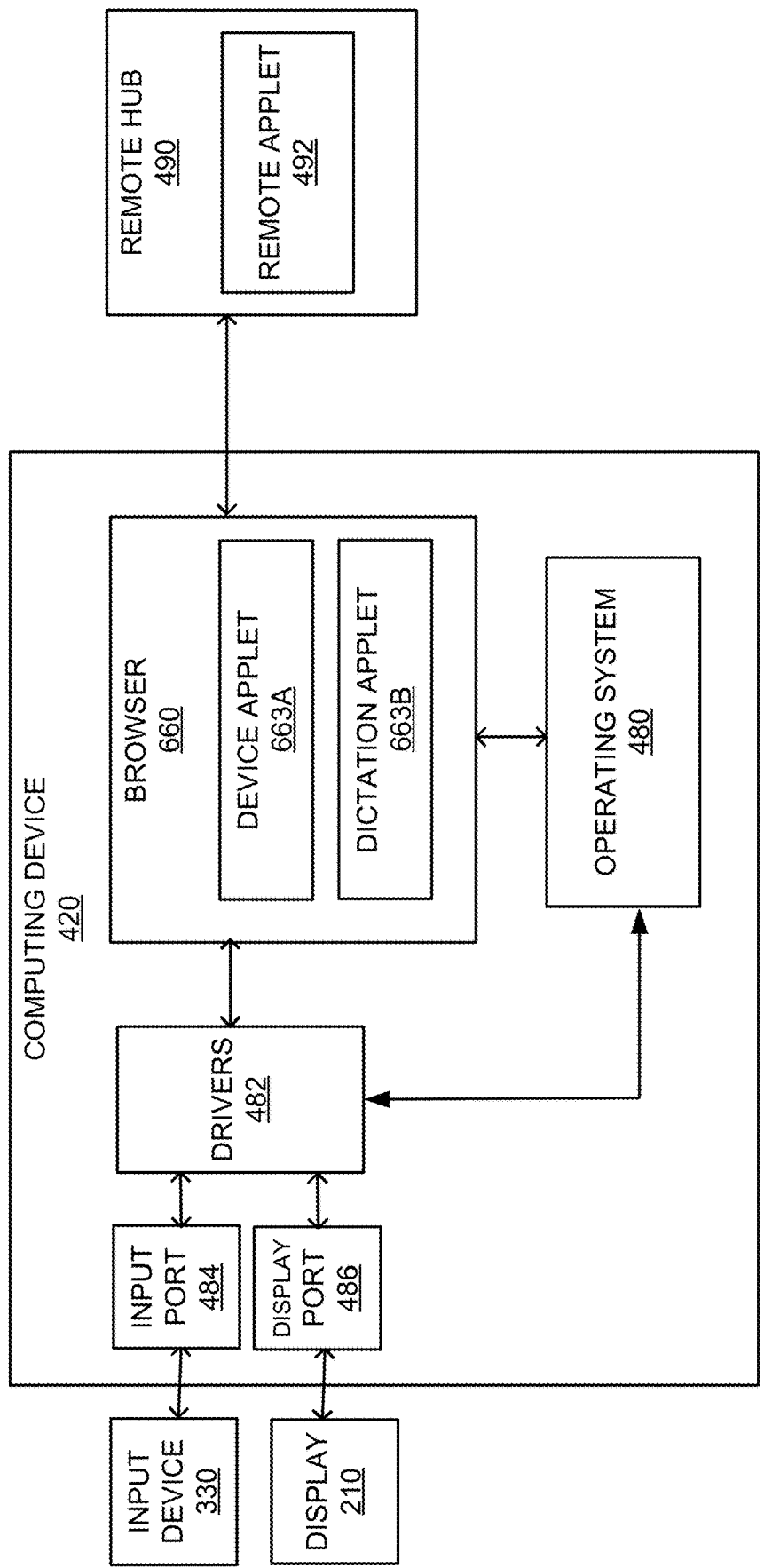
FIG. 4B is a system diagram of illustrating a radiological system for reviewing medical imaging in a browser environment according to some embodiments of the invention.

FIG. 4B is a system diagram of illustrating a radiological system for reviewing medical imaging in a browser environment according to some embodiments of the invention.

The radiological system includes an input device 330 (e.g., a dictation device) and a display 210. The input device 330 and the display 210 may be communicatively coupled to a computing device 420. The computing device 420 may further be communicatively coupled to a remote hub 490.

The computing device 420 may include an input port 484 configured to couple to the input device 330. As discussed further herein, the input device 330 may be a dictation device. The input device 330 may include at least microphone and a plurality of tactile inputs, and may further include any of a number of other functional and/or physical components. Input device 330 may take any physical form and be of any size, shape, color, configuration, etc.

The computing device 420 may further include a display port 486 configured to couple to a display 210. Display 210 may be an output device for presentation of information in visual or tactile form. In some embodiments, display 210 may be an electronic visual display, such as a television screen, computer monitor, and/or video display. Suitable technologies that may be implemented by display 210 include a cathode ray tube display (CRT), a light-emitting diode display (LED), an electroluminescent display (ELD), a plasma display panel (PDP), a liquid crystal display (LCD), a thin-film transistor display (TFT), an organic light-emitting diode display (OLED), and/or the like.

The input port 484 and the display port 486 may be coupled to drivers 482. Drivers 482 may be device drivers that control their associated devices that are attached to the computing device 420. Drivers 482 may provide a software interface to the input device 330 and the display 210, enabling the operating system 480 and/or the browser 660 to access the functions of these devices. Drivers 482 may communicate with the input device 330 and the display 210 through a bus or communications subsystem, for example. In practice, in some embodiments, a user may make an action in browser 660 to invoke input device 330 and/or display 210 that is communicated to the operating system 480. The operating system 480 may then communicate those actions to drivers 480 to invoke a routine in the drivers 482. In some embodiments, a user may make an action in browser 660 to invoke input device 330 and/or display 210 that is communicated directly to the drivers 482 to invoke a routine in the drivers 482. When the operating system 480 and/or the browser 660 invokes a routine in the drivers 482, the drivers 482 issue commands to the input device 330 and/or the display 210.

The operating system 480 may be software that manages the hardware (e.g., input device 330, the display 210, storage, memory, and or the like) and software (e.g., browser 660). The operating system 480 may act as an intermediary between the browser 660 and the hardware in some embodiments, as described above. In other embodiments, the browser 660 may be invoked by the hardware directly. The operating system 480 may be any suitable operating system, including, but not limited to, Microsoft Windows, OS X, Linux (e.g., one example of which is Google Chrome OS), Android, and the like.

Some operating systems that may be implemented as operating system 480, such as Google Chrome OS, may be designed for users that primarily use the Internet (e.g., through browser 660), and as such, may primarily be a web browser with limited ability to run local applications. Instead, some operating systems may rely on Internet applications to accomplish tasks.

As such, browser 660 may implement device applet 663A and/or dictation applet 663B as Internet applications running within browser 660 (e.g., Google Chrome or any other suitable Internet browser application). Browser 660 may be communicatively coupled to a remote hub 490 executing a remote applet 492. The remote hub 490 may be physically located away from the computing device 420, and may include, for example, speech-to-text server 450, medical imaging distribution device 190, and/or any other remote device or server. The computing device 420 may load code into the browser 660 to facilitate communication between the input device 330 and the remote applet 492. Browser 660 may be included within an application layer (as shown and described with respect to FIG. 6), or may be executing on a separate layer above the application layer.

The computing device 420 may perform a variety of functions. The device applet 663A within the browser 660 may identify the input device 330 coupled to the computing device 420 via input port 484. In some embodiments, this identification may be done by exchanging a device identifier corresponding to the input device 330, as described further herein. The device applet may determine a device image that corresponds to the input device 330 (e.g., that matches the input device 330), and select the device image from a plurality of device images that correspond to a plurality of input devices. In some embodiments, some or all of these functions may be partially or wholly executed by remote applet 492 according to instructions sent by the device applet 663A. In these embodiments, remote applet 492 may retrieve the requested information locally or from a remote storage device. The device applet 663A may, either directly or indirectly, invoke drivers 482 to output the device image to the display port 486 to be displayed on display 210. The device image may include one or more graphical representations corresponding to the plurality of tactile inputs of the input device 330.

The device applet 663A may also either obtain or instruct remote applet 492 to obtain a map corresponding to the device image. The map may include a listing of the plurality of tactile inputs of the input device 330 and a listing of one or more actions assignable to each of the plurality of tactile inputs. Each of the one or more actions may correspond to an input to the computing device 420. The device applet 663A may, either directly or indirectly, invoke drivers 482 to output the map to the display port 486 to be displayed on display 210.

A first user input may be made via input device 330 corresponding to a first tactile input of the plurality of tactile inputs of the input device 330. The first user input may be communicated to drivers 482 via input port 484. In response to this first user input, drivers 482 may, directly or indirectly, invoke a routine within device applet 663A to assign a first action of the one or more actions to the first tactile input.

In some embodiments, after at least one action has been assigned to at least one tactile input, the device applet 663A may obtain, either locally or remotely, a medical imaging report. The device applet 663A may send the medical imaging report to the display port 486 via the drivers 482, to be displayed by display 210. A second user input may be made via input device 330 corresponding to the first tactile input of the plurality of tactile inputs of the input device 330. The second user input may be communicated to drivers 482 via input port 484. In response to this second user input, drivers 482 may, directly or indirectly, invoke a routine within device applet 663A to amend the medical imaging report in browser 660 according to the first action assigned to the first tactile input.

In some embodiments, audio input may be received from a microphone of the input device 330 in the form of a dictation and/or voice recording. The audio input may be communicated to drivers 482 via input port 484. In response to this audio input, drivers 482 may, directly or indirectly, invoke a routine within dictation applet 663B to process the dictation using voice recognition, and amend the medical imaging report according to the dictation in the browser 660. In some embodiments, some or all of these functions may be partially or wholly executed by remote applet 492 according to instructions sent by the dictation applet 663B.

Figure 5:
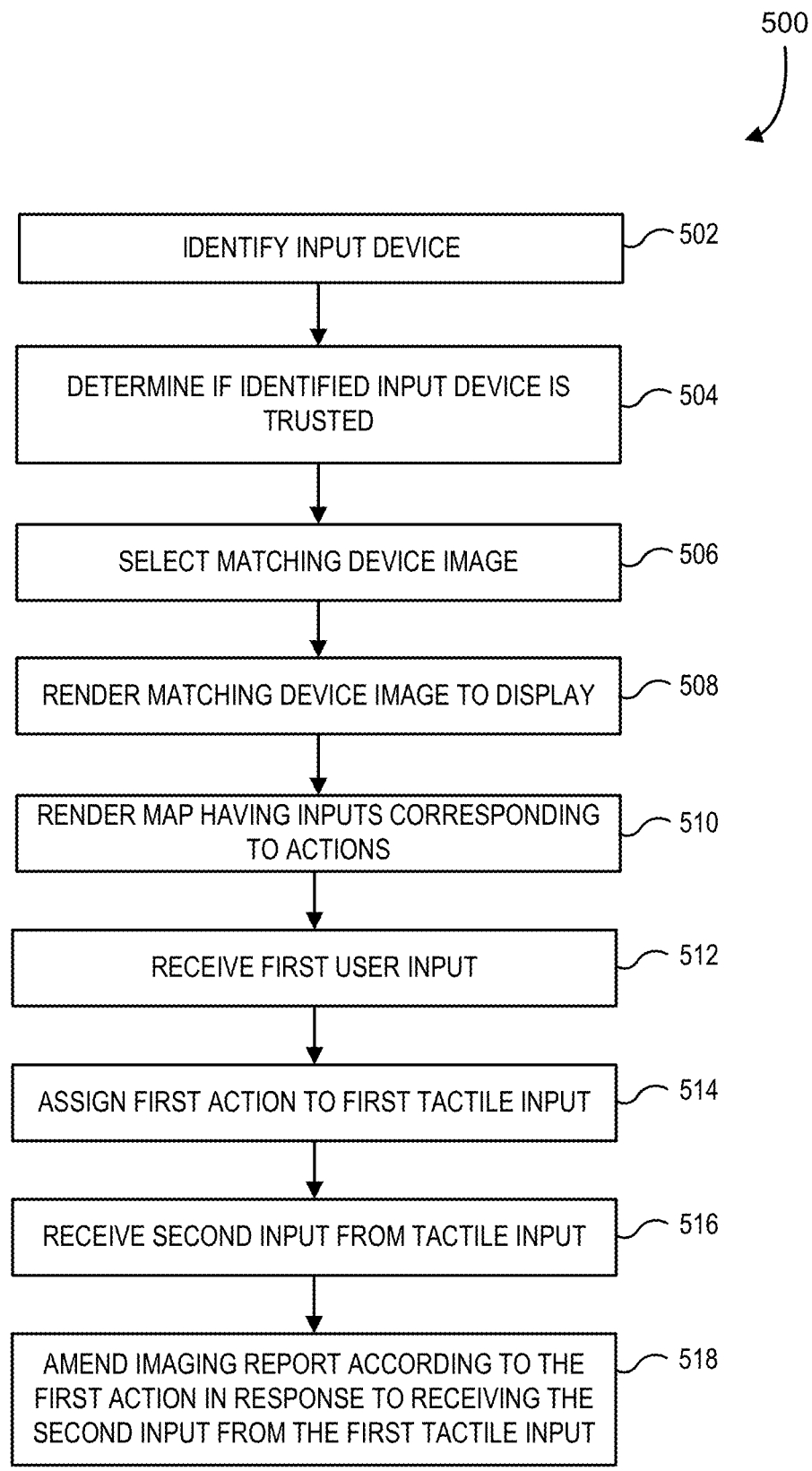
FIG. 5 is a flow chart illustrating a medical imaging report input method according to some embodiments of the invention.

FIG. 5 depicts an illustrative flow chart 500 for a process for medical imaging report input. The process is illustrated as a logical flow diagram, each operation of which represents a sequence of operations that can be implemented in either hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement this process and any other processes described herein.

In process block 502, an input device is identified. In some embodiments, the input device is a recording device and/or a dictation device. In some embodiments, the input device may be identified by computing device 220 and/or 420 by sending a query to the input device over a USB channel and receiving a device identifier from the input device. Optional process block 504 includes determining whether the identified input device is a trusted or supported input device. Computing device 220 and/or 420 may compare the device identifier received from the input device to a list of trusted or supported input devices to determine whether the identified input device is a trusted input device, for example. If the input device is a trusted or supported input device, a matching device image is selected that corresponds to the identified (and trusted or supported) input device, in process block 506. The matching device image may be selected from a plurality of device images that correspond to a plurality of trusted or supported input devices.

In process block 508, the matching device image (e.g., 304) is rendered to the display. The matching device image includes graphical, pictorial and/or symbolic representation of the tactile inputs of the identified input device. A map (e.g., 306) is rendered to the display in process block 510. The map may include a listing of the one or more tactile inputs of the input device and a listing of one or more actions assignable to each of the tactile inputs. Each of the actions may be an input to the computing device (e.g., computing device 220 and/or 420).

In process block 512, a first user input is received. The user input may be from a computer mouse or a computer keyboard, for example. In some embodiments, the user input may be from the input device. The first user input may correspond to a first tactile input of the one or more tactile inputs of the input device. For example, the first user input may be a selection of the graphical image of one of the tactile inputs of the input device and/or a selection of an action to correspond to one of the tactile inputs of the input device. In process block 514, a first action of the one or more actions is assigned to the first tactile input (e.g., 338) in response to the first user input. In one embodiment, a user selects the first action from a drop-down menu to assign the first action to the first tactile input. A medical imaging report may then be rendered to the display in some embodiments. A second user input may be received from the first tactile input of the one or more tactile inputs, in process block 516. For example, the input may be received when the first tactile input is actuated by a user. In process block 518, the medical imaging report is amended according to the first action in response to receiving the second user input from the first tactile input. For example, in response to receiving an actuation of a first tactile input, the medical imaging report may be signed and saved, if the signed and saved action is assigned to the first tactile input.

Figure 6:
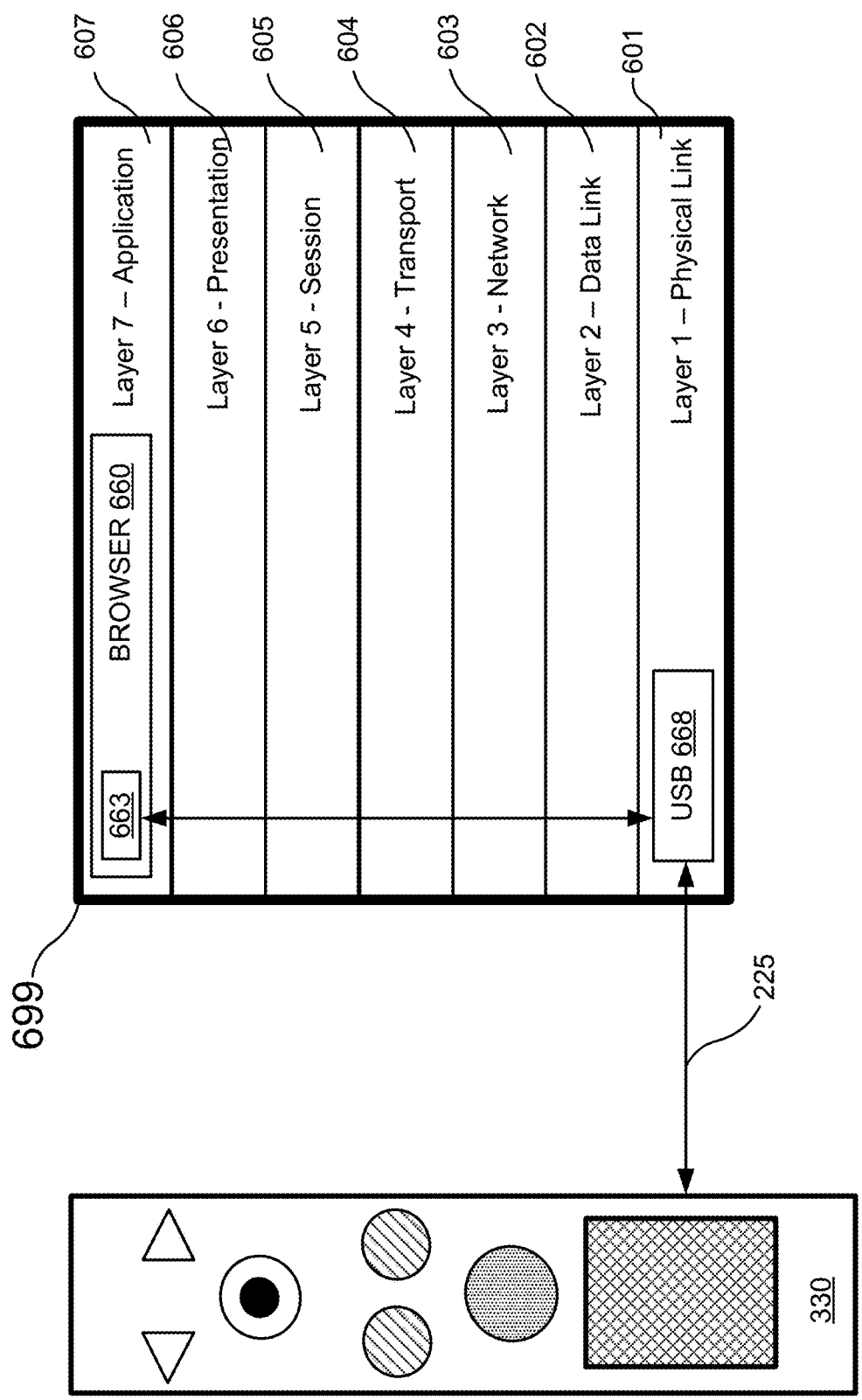
FIG. 6 is an architectural diagram illustrating the functional layers of a medical imaging report input system according to some embodiments of the invention.

FIG. 6 is a block diagram of a protocol stack 699 that may be implemented by the computing device in conjunction with the input device 330, in accordance with some embodiments. The computing device may implement the protocol stack to communicate with any of the other devices described herein. The protocol stack 699 may include one or more of seven layers: an application layer 607, a presentation layer 606, a session layer 605, a transport layer 604, a network layer 603, a data link layer 602, and a physical link layer 601. Together, these seven layers may represent a model, such as an Open Systems Interconnection (OSI) model. The OSI model of FIG. 6 may characterize the communication functions of the computing device. Although shown and described as having seven layers, it is contemplated that the protocol stack 699 may include more or fewer layers to perform less, the same, or additional functions.

According to the OSI model, the application layer 607 may interact with a user (e.g., via receiving user inputs and presenting outputs) and software applications implementing a communication component. The application layer 607 may synchronize communication between entities and determine resource availability. The application layer 607 may be application-specific, in that the specific functions dependent on the particular application being executed by the computing device.

For example, the application layer 607 may execute a browser 660 (e.g., Google Chrome) which in turn may execute the processes (e.g., of flowchart 500) of the disclosure with the assistance of an extension 663. Browser 660 and extension 663 may be executed entirely at the application layer 607. This allows for radiologists who are viewing the medical imaging and mapping their input devices for inputting into medical imaging reports to have a zero footprint system in that only a browser as an application and corresponding extension are required to execute the disclosed processes. In implementations that include a zero footprint system, a list of input devices identifiers, a list of trusted or supported input devices, the plurality of device images (including device image 304), map 306, and user profiles may be stored in a memory of a server, for example. The browser and corresponding extension may then access this content stored in the memory of the server.

The presentation layer 606 may translate between application and network formats. Various applications and networks may implement different syntaxes and semantics. Thus, the presentation layer 606 may transform data from the network into a form that the application accepts. The presentation layer 606 may also format and encrypt data from the application to be sent on a network.

The session layer 605 may control connections between the computing device and other devices and/or servers, as described herein. The session layer 605 may establish the connections, manage the connections, and terminate the connections used to communicate between the devices.

The transport layer 604 may provide techniques for performing quality of service functions during transfers of data between devices. The transport layer 604 may provide error control. For example, the transport layer 604 may keep track of data being transmitted and transmit any communications that fail. In addition, the transport layer 604 may provide an acknowledgment of successful data transmission and send the next data to be transmitted in a synchronous fashion if no errors occurred.

The network layer 603 may provide the means of transferring the data to and from the computing device over a network. The source node and destination node of the devices may each have an address which permits the other to transfer data to it by providing the address with the data. The network layer 603 may also perform routing functions that allow it to a determine a path between the source node and destination node, possibly through other nodes.

The data link layer 602 may define and provide the link between a directly and physically connected source node and destination node. The data link layer 602 may further detect and correct errors occurring at the physical layer 601. In some embodiments, the data link layer 602 may include two sublayers: a media access control (MAC) layer that may control how devices in the network gain access to data and gain permission to transmit it, and a logical link control (LLC) layer that may identify network layer 603 protocols and encapsulate them.

In implementations where input device 330 is a USB device, physical link layer 601 includes a USB port 668 for communicatively coupling to input device 330 via communication link 225. When communicating with input device 330, data from browser 660 propagates through the layers of the protocol stack 699 until it reaches USB port 668, where the signals are sent to input device 330. Similarly, signals received from input device 330 (e.g., a device identifier) propagate through the protocol stack 699 from USB port 668 to browser 660.

As noted, the computer-readable medium may include transient media, such as a wireless broadcast or wired network transmission, or storage media (that is, non-transitory storage media), such as a hard disk, flash drive, compact disc, digital video disc, Blu-ray disc, or other computer-readable media. The computer-readable medium may be understood to include one or more computer-readable media of various forms, in various examples.

In the foregoing description, aspects of the application are described with reference to specific embodiments thereof, but those skilled in the art will recognize that the invention is not limited thereto. Thus, while illustrative embodiments of the application have been described in detail herein, it is to be understood that the inventive concepts may be otherwise variously embodied and employed, and that the appended claims are intended to be construed to include such variations, except as limited by the prior art. Various features and aspects of the above-described invention may be used individually or jointly. Further, embodiments can be utilized in any number of environments and applications beyond those described herein without departing from the broader spirit and scope of the specification. The specification and drawings are, accordingly, to be regarded as illustrative rather than restrictive. For the purposes of illustration, methods were described in a particular order. It should be appreciated that in alternate embodiments, the methods may be performed in a different order than that described.

Where components are described as performing or being "configured to" perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

The various illustrative logical blocks, modules, circuits, and algorithm steps described in connection with the embodiments disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The techniques described herein may also be implemented in electronic hardware, computer software, firmware, or any combination thereof. Such techniques may be implemented in any of a variety of devices such as general purposes computers, wireless communication device handsets, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software modules or hardware modules configured for encoding and decoding, or incorporated in a combined video encoder-decoder (CODEC).

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

What is claimed:

1. A radiological system to facilitate reviewing medical imaging in a browser environment, the radiological system comprising:
    a remote hub that comprises one or more servers and that is remote from a plurality of computing devices communicatively couplable to the remote hub via one or more networks, the remote hub configured to perform:
    processing sets of one or more medical images generated by one or more imaging devices that are remote from the remote hub;
    for each set of one or more medical images of the sets of one or more medical images:
        generating a respective electronic record corresponding to a respective task and including the respective electronic record in a task list, the respective task comprising medical imaging data and medical data identified as relevant to analysis of the medical imaging data; and
        assigning the respective task to a selected queue of a plurality of queues, the selected queue corresponding to a computing device of the plurality of computing devices;
    facilitating amending medical imaging reports corresponding to one or more of the sets of one or more medical images, via a plurality of browser applications of the plurality of computing devices, according to stored assignments of different actions assigned to tactile inputs of a plurality of different dictation devices interfacing with the plurality of computing devices, at least in part by:
    for each computing device of the plurality of computing devices:
        hosting an applet communicatively coupled to a browser application of the plurality of browser applications loaded by the computing device;
        processing a device identifier received from the computing device, the device identifier corresponding to a dictation device communicatively coupled to the computing device;
        matching the received device identifier to a device identifier from a plurality of device identifiers stored by the remote hub;
        consequent to the matching, determining a device image that corresponds to the dictation device to facilitate assignment of one or more actions assignable to one or more tactile inputs of the dictation device and amendment of a medical imaging report corresponding to the respective task received by the computing device; and
        processing the medical imaging report amended based at least in part on the assignment of the one or more actions to the one or more tactile inputs of the dictation device.

2. The radiological system to facilitate reviewing medical imaging in a browser environment as recited in claim 1, where the remote hub is further configured to perform, for each set of one or more medical images of the sets of one or more medical images, consequent to the assigning, transmitting the respective task to the computing device of the plurality of computing devices that corresponds to the selected queue.

3. The radiological system to facilitate reviewing medical imaging in a browser environment as recited in claim 2, where the determining the device image that corresponds to the dictation device comprising selecting the device image from a plurality of device images that correspond to a plurality of dictation devices.

4. The radiological system to facilitate reviewing medical imaging in a browser environment as recited in claim 3, where the remote hub receives the medical imaging report transmitted from the computing device via at least one network of the one or more networks.

5. The radiological system to facilitate reviewing medical imaging in a browser environment as recited in claim 4, where the remote hub saves the assignment of the one or more actions to the one or more tactile inputs of the dictation device in a user profile stored by the remote hub.

6. The radiological system to facilitate reviewing medical imaging in a browser environment as recited in claim 5, where the amendment of the medical imaging report comprising amending the medical imaging report in the browser application in response to receiving user input from at least one of the one or more tactile inputs at least in part by processing a dictation received via a microphone of the dictation device using voice recognition to amend the medical imaging report according to the dictation in the browser application.

7. The radiological system to facilitate reviewing medical imaging in a browser environment as recited in claim 6, where the remote hub is further configured to perform facilitating the assignment with a map corresponding to the device image, the map comprising indicia of the one or more tactile inputs of the dictation device and the one or more actions assignable to the one or more tactile inputs of the dictation device.

8. One or more non-transitory, computer-readable storage devices for storing computer-executable instructions that, when executed by one or more computer systems, configure the one or more computer systems to perform operations comprising:
    processing sets of one or more medical images generated by one or more imaging devices that are remote from the one or more computer systems;
    for each set of one or more medical images of the sets of one or more medical images:

generating a respective electronic record corresponding to a respective task and including the respective electronic record in a task list, the respective task comprising medical imaging data and medical data identified as relevant to analysis of the medical imaging data; and assigning the respective task to a selected queue of a plurality of queues, the selected queue corresponding to a computing device of a plurality of computing devices communicatively couplable to the one or more computer systems via one or more networks; and facilitating amending medical imaging reports corresponding to one or more of the sets of one or more medical images, via a plurality of browser applications of the plurality of computing devices, according to stored assignments of different actions assigned to tactile inputs of a plurality of different dictation devices interfacing with the plurality of computing devices, at least in part by:

for each computing device of the plurality of computing devices:

hosting an applet communicatively coupled to a browser application of the plurality of browser applications loaded by the computing device;

processing a device identifier received from the computing device, the device identifier corresponding to a dictation device communicatively coupled to the computing device;

matching the received device identifier to a device identifier from a plurality of device identifiers stored by the one or more computer systems;

consequent to the matching, determining a device image that corresponds to the dictation device to facilitate assignment of one or more actions assignable to one or more tactile inputs of the dictation device and amendment of a medical imaging report corresponding to the respective task received by the computing device; and processing the medical imaging report amended based at least in part on the assignment of the one or more actions to the one or more tactile inputs of the dictation device.

9. The one or more non-transitory, computer-readable storage devices as recited in claim 8, the operations further comprising:

for each set of one or more medical images of the sets of one or more medical images, consequent to the assigning, transmitting the respective task to the computing device of the plurality of computing devices that corresponds to the selected queue.

10. The one or more non-transitory, computer-readable storage devices as recited in claim 9, where the determining the device image that corresponds to the dictation device comprising selecting the device image from a plurality of device images that correspond to a plurality of dictation devices.

11. The one or more non-transitory, computer-readable storage devices as recited in claim 10, where the one or more computer systems receive the medical imaging report transmitted from the computing device via at least one network of the one or more networks.

12. The one or more non-transitory, computer-readable storage devices as recited in claim 11, the operations further comprising saving the assignment of the one or more actions to the one or more tactile inputs of the dictation device in a user profile stored by the one or more computer systems.

13. The one or more non-transitory, computer-readable storage devices as recited in claim 12, where the amendment of the medical imaging report comprising amending the medical imaging report in the browser application in response to receiving user input from at least one of the one or more tactile inputs at least in part by processing a dictation received via a microphone of the dictation device using voice recognition to amend the medical imaging report according to the dictation in the browser application.

14. The one or more non-transitory, computer-readable storage devices as recited in claim 13, the operations further comprising facilitating the assignment with a map corresponding to the device image, the map comprising indicia of the one or more tactile inputs of the dictation device and the one or more actions assignable to the one or more tactile inputs of the dictation device.

15. A method to facilitate reviewing medical imaging in a browser environment, the method comprising:

processing sets of one or more medical images generated by one or more imaging devices that are remote from one or more computer systems;

for each set of one or more medical images of the sets of one or more medical images:

generating a respective electronic record corresponding to a respective task and including the respective electronic record in a task list, the respective task comprising medical imaging data and medical data identified as relevant to analysis of the medical imaging data; and assigning the respective task to a selected queue of a plurality of queues, the selected queue corresponding to a computing device of a plurality of computing devices communicatively couplable to the one or more computer systems via one or more networks; and facilitating amending medical imaging reports corresponding to one or more of the sets of one or more medical images, via a plurality of browser applications of the plurality of computing devices, according to stored assignments of different actions assigned to tactile inputs of a plurality of different dictation devices interfacing with the plurality of computing devices, at least in part by:

for each computing device of the plurality of computing devices:

hosting an applet communicatively coupled to a browser application of the plurality of browser applications loaded by the computing device;

processing a device identifier received from the computing device, the device identifier corresponding to a dictation device communicatively coupled to the computing device;

matching the received device identifier to a device identifier from a plurality of device identifiers stored by the one or more computer systems;

consequent to the matching, determining a device image that corresponds to the dictation device to facilitate assignment of one or more actions assignable to one or more tactile inputs of the dictation device and amendment of a medical imaging report corresponding to the respective task received by the computing device; and processing the medical imaging report amended based at least in part on the assignment of the one or more actions to the one or more tactile inputs of the dictation device.

16. The method to facilitate reviewing medical imaging in a browser environment as recited in claim 15, further comprising:

for each set of one or more medical images of the sets of one or more medical images, consequent to the assigning, transmitting the respective task to the computing device of the plurality of computing devices that corresponds to the selected queue.

17. The method to facilitate reviewing medical imaging in a browser environment as recited in claim 16, where the determining the device image that corresponds to the dictation device comprising selecting the device image from a plurality of device images that correspond to a plurality of dictation devices.

18. The method to facilitate reviewing medical imaging in a browser environment as recited in claim 17, where the one or more computer systems receive the medical imaging report transmitted from the computing device via at least one network of the one or more networks.

19. The method to facilitate reviewing medical imaging in a browser environment as recited in claim 18, further comprising saving the assignment of the one or more actions to the one or more tactile inputs of the dictation device in a user profile stored by the one or more computer systems.

20. The method to facilitate reviewing medical imaging in a browser environment as recited in claim 19, where the amendment of the medical imaging report comprising amending the medical imaging report in the browser application in response to receiving user input from at least one of the one or more tactile inputs at least in part by processing a dictation received via a microphone of the dictation device using voice recognition to amend the medical imaging report according to the dictation in the browser application.

* * * * *